US005340834A

United States Patent [19]

Stitt

[11] Patent Number: 5,340,834

[45] Date of Patent: Aug. 23, 1994

[54] METHOD OF INCREASING MUSCLE MASS IN CHICKENS

[76] Inventor: Paul A. Stitt, 123 Cleveland Ave., Manitowoc, Wis. 54220

[21] Appl. No.: 743

[22] Filed: Jan. 5, 1993

[51] Int. Cl.$^5$ .............................................. A61K 31/28
[52] U.S. Cl. ................................................... 514/505
[58] Field of Search ......................... 514/505; 424/655

[56] References Cited

PUBLICATIONS

Chemical Abstracts (116:17289a) 1991.
Paul et al., Zivocisna Vyroba 1991, pp. 525–535.

*Primary Examiner*—Marianne M. Cintins
*Assistant Examiner*—K. Weddington
*Attorney, Agent, or Firm*—Sughrue, Mion, Zinn, Macpeak & Seas

[57] ABSTRACT

A method for increasing muscle mass and decreasing fat in chickens which includes administering orally to a chicken, a biologically effective amount of chromium citrate.

10 Claims, No Drawings

METHOD OF INCREASING MUSCLE MASS IN CHICKENS

FIELD OF THE INVENTION

The present invention relates to a method of increasing muscle content and reducing fat content in chickens by administering a water soluble chromium chelate. In particular, the present invention is directed to a method of increasing feed efficiency in chickens by adding chromium citrate to the diet.

BACKGROUND OF THE INVENTION

The occurrence and function of chromium in biological systems was first described by Dr. Walter Mertz at the Human Nutrition Laboratory in Bethesda, Md. (see, *Physiological Rev.* 49: 163, 1969).

It has been proposed by Dr. Richard Anderson of the USDA, that signs of chromium deficiency are impaired glucose tolerance, elevated fasting insulin, glycosuria, decreased insulin receptor numbers, and elevated cholesterol and triglycerides in hypoglycemia. Decreased sperm count and sterility have been observed in experimental animals, but not humans. Dr. Anderson has stated that these symptoms, usually associated with aging, may actually be the result of long term low chromium diets (see, *The Science of the Total Environment* vol. 86, p. 75–81 (1989)). Chromium picolinate, a fat soluble chelate of chromium, was shown by Dr. Gary Evans to improve body composition and weight loss in healthy adults (see, *Int. J. Biosocial Medical Research,* vol. 13 (2) 1989.

U.S. Pat. No. 4,315,927 discloses the use of chromium picolinate to increase chromium assimilation. The reference discloses that chromium picolinate is not soluble. Further, chromium picolinate is expensive.

U.S. Pat. No. 4,918,102 discloses the use of GTF (glucose tolerance factor) and chromium picolinate to prevent hypoglycemia and alcoholism. GTF is a factor made by the human body that contains chromium, which is more available to the body.

U.S. Pat. No. 4,925,855 discloses the use of synthetic GTF. GTF is an extremely large complex of chromium with two molecules of niacin and at least one amino acid. However, the exact structure of the mechanism of release of the chromium is unknown.

U.S. Pat. No. 4,571,391 discloses the use of chromium acetylacetonate for treating diabetes. The reference further discloses the use of 7 to 70 μg of chromium per Kg of body weight per dose. This corresponds to a dose of 490 to 4900 μg for a 70 Kg person. The reference further discloses the use of up to 4 doses per day.

*Archives of Biochemistry and Biophysics,* vol. 85, p. 293 (1959) discloses that very stable chromium complexes of bidentate chromium acetylacetonate seem to be metabolically inert.

Mertz, *Nutrition Reviews* vol. 33, No. 5, p. 130 (May 1975) discloses that "simple chromium" compounds like chromium chloride or chromium acetate, which are chromium complexes, do not meet the criteria of absorption and bioavailability needed for use as cofactors in insulin.

U.S. Pat. No. 4,335,116 discloses the use of at least two organic, metal ion complexing agents for parenteral administration. However, the reference does not disclose using chromium citrate. Further, the reference discloses using extremely high doses of 500 ppm of chromium.

U.S. Pat. No. 4,684,637 discloses the use of chromium protoporphyrin to inhibit the metabolism of heme to bilirubin.

A major drawback in the chicken industry is the low amount of meat produced per pound of feed consumed by the chicken. A considerable amount of feed is wasted in the form of feces and fat produced. The amount of feed is a major cost factor in raising chickens, and the amount of meat produced is the only product of value. Therefore, there is a need in the industry for increasing the amount of meat produced per pound of feed consumed.

SUMMARY OF THE INVENTION

Accordingly, one object of the present invention is to provide a method of improving the feed efficiency of chickens by adding chromium to the diet in such a way that it is readily used by the animal's digestive system. Animal feeds, such as chicken feeds are known to contain from 1,000 to 15,000 ppb of chromium. The chromium level is dependent upon the level of calcium compounds added to the feed, since chromium salts are a common contaminant in most calcium sources.

I have discovered that by adding as little as 1 ppb of chromium citrate to feeds containing up to 15,000 ppb chromium, a substantial increase in the meat content per pound can be achieved even though the percentage increase in chromium in the diet is very small. Other water soluble forms of chromium, such as chromium chloride, have been found to be ineffective in achieving this goal.

Accordingly, a further object of the present invention is to provide a composition and method for supplementing the essential metal chromium in a water soluble form in the drinking water of chickens, and for facilitating the absorption of the chromium by the intestinal cells.

It is also an object of the present invention to correct predetermined metal deficiency in avians and to eliminate the symptoms of these deficiencies without concurrently reducing the assimilated levels of other essential minerals.

Still another object of the present invention is the administration of chromium in a safe, physiological form. In this way, deficiencies can be therapeutically eliminated without the need for pharmacological doses, even when caused by malabsorption of other forms of chromium.

Yet another object of the present invention is the administration of supplemental chromium in a form which is simple to produce and economically feasible to use in chicken diets.

These objects are attained by a method of increasing muscle mass in a chicken comprising administering to the chicken a biologically effective amount of chromium citrate.

Other objects and advantages of the present invention will be readily apparent to one of ordinary skill in the art from the following description.

DETAILED DESCRIPTION OF THE INVENTION

The chromium citrate used in the present invention is a chelated form of chromium III with citric acid. The resulting chelate complex is soluble in water, and I theorize that citrate is bound strongly enough to the chromium to prevent chromium from forming chromium polymers in aqueous solutions. When chromium forms chromium polymers in aqueous media, as it does then chromium chloride is dissolved in water, the chromium bound in the polymers is mostly unavailable. The citric acid acts as a strong anionic chelating agent, capable of binding the cation (chromium) and holding it available for enzymatic reactions.

This chromium complex can be prepared by the simple method of adding equimolar amounts of citric acid or tri-sodium citrate to chromium trichloride or chromium sulfate in distilled water. The chromium chelates form within minutes, even at room temperature. The solution is clear, indicating 100% solubility.

When administered orally, chromium citrate will generally be incorporated into the drinking water. The desirable concentration of chromium citrate in the drinking water is from 0.1 ppb to 100 ppb, preferably 0.2 ppb to 50 ppb, and most preferably, from 0.25 ppb to 10 ppb. The water can be provided ad lib. The chromium citrate can be added from birth or can be added at a later time. The longer the time used, the better the results.

The chromium citrate is made up in a concentrated solution of 1 to 50 million ppb and is diluted to the proper level when used. Ratio controlled pumps can be used to add the chromium citrate concentrate to the water line being used to water the chickens to properly dilute the chromium citrate solution.

The chromium citrate aqueous concentrate can also be sprayed onto dry feed and consumed in that manner. As a practical matter, the chromium citrate is formed in water at 10 to 50 million ppb. It is then sprayed onto any dry carrier to reduce the concentration to several thousand ppb. Then the dried material can be easily mixed with dry feed to achieve the proper concentration. This method is used for the convenience of the feed operator. Any safe and efficacious method can be used to reduce the concentration of the chromium citrate form the preparation level to the user level. The desirable concentration in the feed is from 1 ppb to 500 ppb, preferably 5 to 100 ppb and most preferably 10 to 50 ppb.

Alternatively, the chromium citrate coordination complexes may be administered in the form of tablets along with a suitable carrier using any known technique. The daily dose would vary from 0.1 microgram for very young chicks to 5 micrograms for older chickens.

The chromium chelate may be administered singly or in combination with any other chelates in the diet, such as zinc proteinate or chromium picolinate. The primary advantage of chromium chelate is that the chelate is efficiently used and permits precise, preselected control over assimilation of the chromium. Because of the low lever of chromium used in this procedure, this procedure is much safer than those that use much higher levels of chromium.

EXAMPLES

The following examples are provided for illustrative purposes, but the examples are in no way intended to limit the scope of the present invention in any way.

Synthesis Example 1

Preparation of Chromium Citrate 222 g of chromium III chloride were dissolved in 3 liters of distilled water. 160 g of citric acid were added. This produces a concentration of 14.4 million ppb of chromium citrate. After 10 minutes of stirring at room temperature, the green color changed to purple, signifying that chromium citrate has been formed. Then, 3 ml of the resulting chromium citrate were added to 1 gallon of distilled water. The following amounts of the above solution were prepared:

TABLE 1

| Ml of Concentrate Added to 3 Gallons of Tap Water | ppb of Chromium in Drinking Water |
|---|---|
| 1 | 1 |
| 2 | 2 |
| 8 | 8 |
| 16 | 16 |
| 32 | 32 |
| 64 | 64 |

By this method, various amounts of chromium citrate in varying concentrations were obtained.

TABLE 2

| Broiler Grower Feed Formula-19% Protein | |
|---|---|
| Ingredient | Amount |
| Corn | 60 pounds |
| Soy bean meal | 25 pounds |
| Ground Oats | 5 pounds |
| Stabilized flax | 3.5 pounds |
| Nutritional yeast | 1.0 pounds |
| Alfalfa meal | 2.0 pounds |
| D,L-methionine | 1 oz. |
| Dicalcium phosphate | 1.5 pounds |
| Limestone | 1.0 pounds |
| Salt | 4.0 oz. |
| Vitamin premix (manufactured by McNess) | 8.0 oz. |

The background level of chromium in the control and experimental diet was 1000 ppb. Using conventional feedstuffs, I could not obtain any lower background level of chromium.

Application Example I 98 chickens were divided evenly into 7 groups of 14 each. All chickens were given the same feed. Table 1 lists the amount of each ingredient in the diet used. The chickens were given the prescribed drinking water (with chromium added) from birth. The results show a 1 ppb concentration of chromium citrate in the drinking water produces a 25% increase in pounds of chicken per pound of feed. All levels of chromium used produce a larger bird than the control diet in the same amount of time.

TABLE 3

| Factors | Sample No. 1 | Sample No. 2 | Sample No. 3 | Sample No. 4 | Sample No. 5 | Sample No. 6 | Sample No. 7 |
|---|---|---|---|---|---|---|---|
| Chromium citrate conc. (ppb) | 0 | 1 | 2 | 8 | 16 | 32 | 64 |
| Numbers of chickens | 14 | 14 | 14 | 14 | 14 | 14 | 14 |
| Total feed consumed (lbs.) | 172 | 168 | 184 | 171 | 187 | 222 | 175 |

TABLE 3-continued

| Factors | Sample No. 1 | Sample No. 2 | Sample No. 3 | Sample No. 4 | Sample No. 5 | Sample No. 6 | Sample No. 7 |
|---|---|---|---|---|---|---|---|
| Total live wt. of chickens (lbs) | 68.6 | 83.4 | 81.5 | 77.1 | 76.4 | 76.8 | 72.3 |
| Average live wt. (lbs) | 4.90 | 5.96 | 5.82 | 5.51 | 5.46 | 5.49 | 5.16 |
| Pounds of live weight per pound of feed | .399 | .497 | .443 | .451 | .409 | .346 | .413 |
| Feed efficiency percent improvement over control | 0 | 25% | 11% | .3% | 2.5% | −15% | 3.5% |
| Deboned wt. yield of meat (lbs) | 1.42 | 1.68 | 1.88 | 1.85 | 1.62 | 1.64 | 1.58 |
| Percent improvement over control | 0 | 18% | 32% | 30% | 14% | 15% | 11% |

As shown from the preceding example, all chromium levels used produced a larger bird than the control diet (Sample No. 1) in the same amount of time. The chromium citrate in the diet increased the deboned meat yield by 11 to 32%. The results show that, in particular, 1 ppb of chromium citrate produced a 25% increase in chickens meat produced per pound of feed over control.

While the invention has been described in detail and with reference to specific embodiments thereof, it will be apparent to one skilled in that art that various changes and modifications can be made without departing from the spirit and scope of the invention.

What is claimed is:

1. A method of increasing muscle mass in a chicken, comprising administering to the chicken a biologically effective amount of chromium citrate.

2. A method of increasing muscle mass in a chicken as in claim 1, wherein said administering is carried out by adding chromium citrate to the chicken's drinking water.

3. A method of increasing muscle mass in a chicken as in claim 2, wherein the biologically effective amount is from about 0.1 ppb to about 100 ppb in the chicken's drinking water.

4. A method of increasing muscle mass in a chicken as in claim 3, wherein the biologically effective amount is from about 0.2 ppb to about 50 ppb in the chicken's drinking water.

5. A method of increasing muscle mass in a chicken as in claim 4, wherein the biologically effective amount is from about 0.25 ppb to about 10 ppb in the drinking water.

6. A method of increasing muscle mass in a chicken as in claim 1, wherein said administering is carried out by adding chromium citrate to the chicken's feed.

7. A method of increasing muscle mass in a chicken as in claim 6, wherein the biologically effective amount is from about 1 to 100 ppb in the chicken's feed.

8. A method of increasing muscle mass in a chicken as in claim 7, wherein the biologically effective amount is from about 5 to 80 ppb in the chicken's feed.

9. A method of increasing the muscle mass in a chicken as in claim 8, wherein the biologically effective amount is from about 10 to 50 ppb in the chicken's feed.

10. A method of increasing muscle mass in a chicken as in claim 1, wherein said administering is carried out by supplying the chromium citrate in a tablet.

* * * * *